United States Patent [19]

Azarnia et al.

[11] Patent Number: 5,607,565
[45] Date of Patent: Mar. 4, 1997

[54] APPARATUS FOR MEASURING ANALYTES IN A FLUID SAMPLE

[75] Inventors: Roobik Azarnia, South Miami; Susan M. Fuentes, Princeton; Thomas R. Russell, Miami, all of Fla.

[73] Assignee: Coulter Corporation, Miami, Fla.

[21] Appl. No.: 410,997

[22] Filed: Mar. 27, 1995

[51] Int. Cl.⁶ ........................................... G01N 27/26
[52] U.S. Cl. ................ 204/403; 204/409; 204/415; 204/412; 204/401; 422/68.1; 422/82.02; 422/82.03; 435/4; 435/14; 435/817; 435/287.1; 436/52
[58] Field of Search ..................... 204/403, 409, 204/153.12, 415, 153.17, 401, 412; 422/68.1, 82.01, 82.03; 435/4, 14, 291, 288, 817; 436/52

[56] References Cited

U.S. PATENT DOCUMENTS

| | | | |
|---|---|---|---|
| 3,539,455 | 11/1970 | Clark, Jr. | 204/403 |
| 3,839,153 | 10/1974 | Schuurs et al. | 195/103.5 |
| 3,979,274 | 9/1976 | Newman | 204/195 |
| 4,040,908 | 8/1977 | Clark, Jr. | 195/103.5 |
| 4,342,739 | 8/1982 | Kakimi et al. | 424/1 |
| 4,483,928 | 11/1984 | Suzuta et al. | 436/519 |
| 4,985,125 | 1/1991 | Watanabe et al. | 204/415 |
| 5,352,348 | 10/1994 | Young et al. | 204/415 |
| 5,429,726 | 7/1995 | Johnson et al. | 204/153.12 |

FOREIGN PATENT DOCUMENTS

| | | |
|---|---|---|
| 2029013 | 5/1979 | United Kingdom . |
| 85/02017 | 5/1985 | WIPO . |
| 86/07150 | 12/1986 | WIPO . |
| 92/00515 | 1/1992 | WIPO . |

OTHER PUBLICATIONS

*YSI Model 2300 STAT Glucose & L-Lactate Analyzer Operations Manual*; Yellow Springs Instrument Co., Inc.; pp. i–iii, 2.1–2.8, 5.1–5.4, 6.3–6.4.

Primary Examiner—Bruce F. Bell
Attorney, Agent, or Firm—Anibal Jose Cortina; Warren W. Kurz

[57] ABSTRACT

A method and apparatus provide a system for measuring a measurable component in a sample. A sample is introduced into a chamber. A permeable membrane to the measurable component allows the component to pass into a second chamber. In the second chamber the component is measured directly or reacted in the presence of an enzyme to generate a detectable product detected by a detector therein. The second chamber is then flushed. The second chamber is only of a size sufficient to contain enough liquid to wet the detector therein.

14 Claims, 8 Drawing Sheets

APPARATUS FOR MEASURING ANALYTES IN A FLUID SAMPLE

The present invention is related to improvements in apparatus for analyzing a fluid sample for the presence of a measurable component or analyte. More particularly, the invention is directed to an improved "biosensor" for sensing an analyte of the type which, upon being contacted with an enzyme, produces an enzymatic reaction in which a more readily detectable substance is produced in proportion to the concentration of the analyte being sensed. The apparatus of the invention is particularly useful, for example in detecting the amount of glucose in a whole blood sample.

In the past, considerable efforts have been devoted to improving analytical techniques for use in biomedical applications, including clinical diagnosis, as well as for research and industrial applications. Among these techniques are those conducted with electrochemical, e.g., amperometric, sensing devices. When these devices sometimes known as "biosensors" were first developed, they received widespread attention due to their potential use in analysis of clinical chemical assays and in other types of commercial applications. Electrochemical sensing devices have become quite popular in the medical field for measurement of various substances. In addition, enzymes have been used in conjunction with such devices cells, especially in instances where the unknown substance to be measured is not sufficiently electrochemically active to be detectable, but a material produced or consumed by an enzymatic reaction with that unknown substance is detectable.

For example, it is known that glucose alone does not generate a detectable electrochemical signal when tested in an electrochemical device. However, glucose is electrochemically detectable under the following conditions described herein. Specifically, it is known that a detectable signal can be generated from the following reaction which takes place in the presence of the enzyme glucose oxidase (GO):

$$\text{Glucose} + 2H_2O + O_2 \xrightarrow{GO} \text{Gluconic acid} + H_2O_2$$

The resulting hydrogen peroxide ($H_2O_2$) is electrochemically detectable and the amount of hydrogen peroxide generated and detected is directly proportional to the amount of glucose or substrate present. In light of the relationship between the amount of hydrogen peroxide generated and the glucose, the amount of glucose in the sample can then be calculated.

With this relationship in mind, it is noted that glucose is a particularly important substance to measure in a number of different types of analyses. For instance, the measure of glucose in whole blood is often critical to the diagnosis and treatment of diabetes.

In conducting measurements of glucose, it has been suggested that a pH sensitive electrode can be used to detect the gluconic acid produced by the enzymatic reaction of glucose oxidase with glucose. It is known from such a system that the enzyme can be trapped between a pair of cuprophane membranes. This can occur because the glucose diffuses through the membrane and is converted by the enzyme to gluconic acid, which then diffuses toward the pH sensitive electrode for detection thereby.

Alternatively, it has been suggested that by using a hydrophobic membrane (a dialysis membrane), glucose oxidase, and an oxygen electrode, a biosensor system can be constructed that is sensitive to glucose. See, for example, the disclosure of U.S. Pat. No. 4,985,125. In such a system, the amount of oxygen consumed in the above reaction is proportional to the glucose content of the glucose solution.

The consumption of oxygen is detected by the oxygen electrode and a signal indicative of the amount of glucose present is generated. It is noted that in these types of oxygen detecting systems the detecting electrode is typically made of platinum and has a negative polarity with respect to a reference electrode.

Alternatively, such electrodes are also used to detect hydrogen peroxide generated from glucose when the polarity of the detecting electrode (Pt) is reversed to positive. This is in contrast to the above-discussed systems which provide for measurement of pH change or oxygen consumed. In the hydrogen peroxide detecting system an enzyme is placed on the detecting electrode, i.e., anode side of a cellophane membrane. The low molecular weight glucose passes through the membrane and reacts with the enzyme, but interfering high molecular weight substances such as catalase do not pass through. The enzyme(s) are held in place (i.e. immobilized) by a thin film located directly between the platinum surface of the electrode and the membrane; thus, the enzyme is sandwiched, and thereby trapped, between a pair of spaced semi-permeable membranes. See, for example, the biosensor disclosed in U.S. Pat. No. 5,429,726.

In systems of the above type, since the cellophane membrane will not prevent low molecular weight interfering materials, such as uric acid, or ascorbic acid from reaching the anode. It has been suggested that a dual electrode system can be employed to adjust the measurement for the effects caused by such interfering materials. The dual electrode system would include a compensating electrode, without an enzyme present, which provides a signal representative of the interfering substances while an electrode in the presence of the enzyme detects both the hydrogen peroxide and the signal caused by the interfering substances. By subtracting the reading of the compensating electrode from that of the electrode in the presence of the enzyme, the amount of hydrogen peroxide production, and, thus, the concentration of glucose in a sample can be determined.

As noted above, it is common to entrap the enzyme component of certain biosensor between a pair of membranes. Such an arrangement provides the advantage that the enzymes are then reusable. However, by immobilizing the enzymes and repeatedly using them in multiple tests, there results a loss of enzyme activity, requiring frequent replacement. Further, immobilization results in a limited enzyme life requiring extensive and sometimes complex retrofitting of an instrument in which they are employed. Another disadvantage is that the immobilized enzyme concentration cannot be varied to adapt to different reactions and reaction rates. Ultimately, the membranes immobilizing the enzyme foul, also resulting in fouling of the electrode and resulting in deterioration of the signal produced. The entire assembly of the membrane and immobilized enzyme must then be replaced in an often complex operation.

SUMMARY OF THE INVENTION

In accordance with the invention there is provided an apparatus which avoids the disadvantages characteristic of the presently known methods and devices. The invention requires only a relatively small amount of liquid reagent, e.g., enzyme, while providing a high sample throughput, i.e., short recovery time.

The apparatus of the invention also provides the advantages and stability of an immobilized enzyme system with the flexibility of a liquid enzyme system, and without the disadvantages inherent in an immobilized enzyme system.

As implemented in one aspect, the apparatus of the invention utilizes the flow of small volumes of liquid, i.e., microflow, to remove substances being detected from a measurement or detecting chamber. This allows rapid recovery and accurate measurement of a desired component in subsequent samples because the initial signal can be quickly washed away and is no longer detected. All of this is done in a consistently repeatable manner from one sample to the next.

As used herein, the phrase "small volumes of liquid" and "microflow" are interchangeable and used to identify the volumes of liquid advantageously used for the practice of some embodiments of the invention. For purposes of this disclosure, this term means volumes of liquid on the order of microliters, typically anywhere from about 1 microliter to about 1,000 microliters, more typically, about 10 to about 100 microliters.

The apparatus of the invention also facilitates maintaining signal detectors employed in a clean condition and, as noted above, in contrast to immobilized enzyme systems, allows optional reuse and varying of enzyme concentrations employed to provide a greater amount of analysis flexibility. Further, in accordance with the invention, high enzyme activity can be maintained over time without requiring complicated and expensive replacing of parts, for example, as may be required in an immobilized enzyme system due to fouling of the membranes holding the immobilized enzymes or due to a build up of other substances within the immobilized enzyme system.

In accordance with the present invention, there is provided an improved biosensor apparatus for measuring the amount of a specific analyte in a liquid sample, for example, the amount of glucose in a whole blood sample. The apparatus of the invention comprises a housing defining first and second chambers separated by a semipermeable membrane which is adapted to pass or transmit the analyte to be measured. The first chamber has an inlet for admitting the liquid sample into the first chamber. The second chamber is adapted to contain a liquid reagent which is capable of either carrying the analyte in solution or suspension, or of reacting with the analyte to produce a measurable byproduct. A detector is provided to detect either the analyte in solution, or the measurable byproduct (e.g. hydrogen peroxide). The apparatus of the invention differs form the aforementioned prior art in that (i) the second chamber has an inlet for selectively admitting the analyte-reactive (or dissolving) substance; (ii) the detector is located within the second chamber; and (iii) means are provided for flushing the second chamber of analyte, substance, and/or byproduct, whereby the apparatus is readily reusable.

BRIEF DESCRIPTION OF THE DRAWINGS

The invention will be more readily understood by reference to the accompanying drawings wherein.

DETAILED DESCRIPTION OF THE INVENTION

Figure 1:
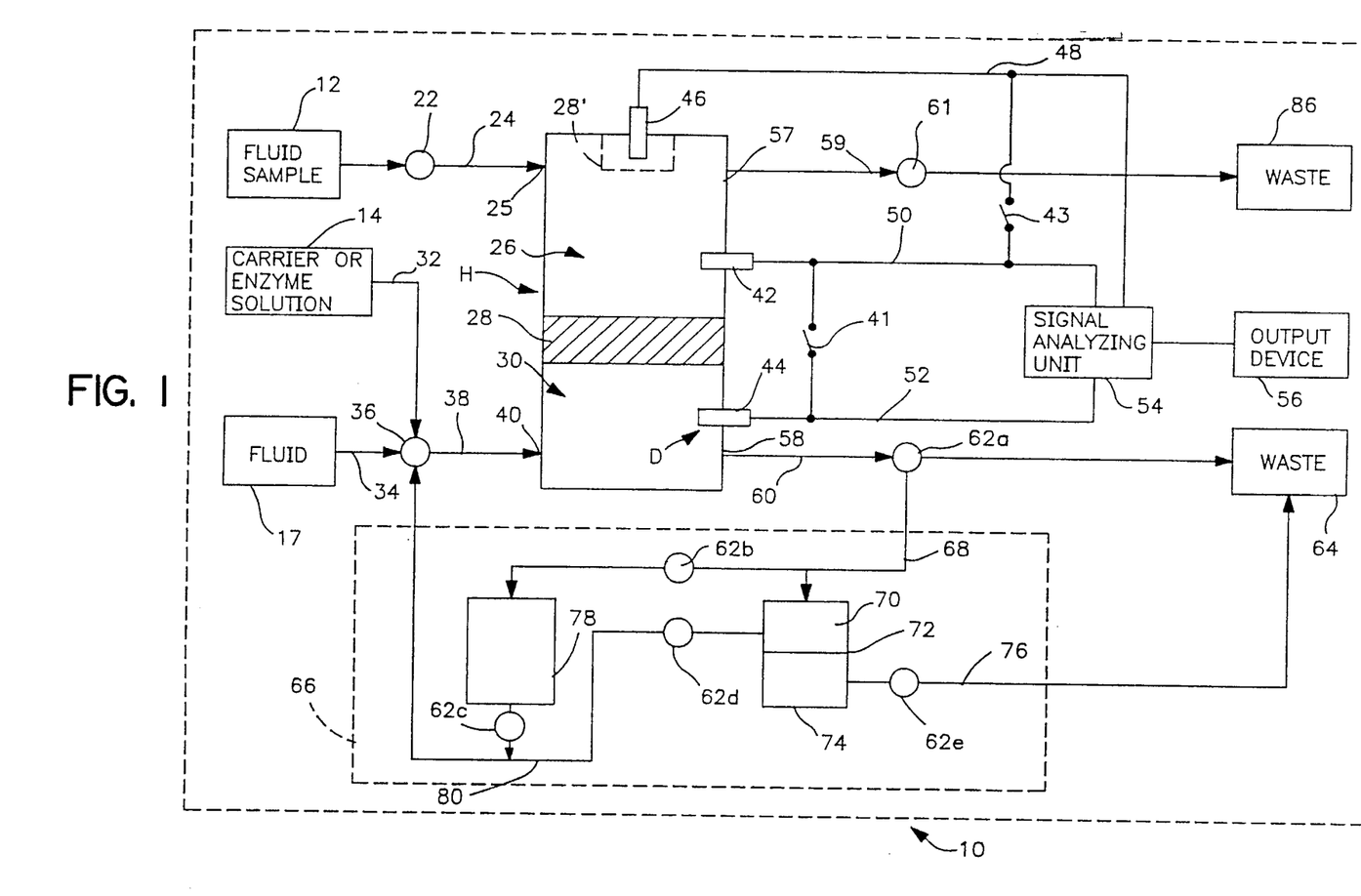
FIG. 1 is a schematic diagram of a detailed embodiment of an analyzer according to the present invention.

Referring to FIG. 1 of the drawings, a first embodiment of the microflow analyzing apparatus 10 of the invention is schematically illustrated. In its simplest form, such apparatus comprises a housing H which defines a sample supply chamber 26 and an analyte measurement chamber 30, such chambers being separated by a single semipermeable membrane 28. While schematically illustrated as being of similar sizes, chamber 30 is significantly smaller than chamber 30. A fluid sample 12 containing an analyte to be measured is loaded into chamber 26 via an inlet line 24 and a chamber inlet 25. As the sample enters the sample supply chamber 26, predetermined components (analytes) having a specific size diffuse through the membrane and enter the measurement chamber 30 for interaction with a fluid reagent contained therein. The latter may comprise either a simple carrier for the analytes being measured, or alternatively an enzyme solution which is adapted to react with the analytes to produce a detectable byproduct. The fluid reagent, which is provided by a source 14, is loaded into measurement chamber 30 via a first inlet line 32, a mixing valve 36, a second inlet line 38 and a chamber inlet 40. A detector D located within chamber 30 operates to either directly detect the analyte in the carrier solution, or to detect the reaction byproduct produced by the enzyme in the fluid reagent and the analyte passed by the membrane.

As shown in FIG. 1, an enzyme solution 14 may be loaded through the enzyme inlet line 32 through the valve 36 and the second chamber inlet line 38 into the second chamber inlet 40 to be received in the second chamber 30. Optionally, in one specific embodiment, depending on the substances and enzymes loaded into the chambers 26 and 30, if an enzyme solution 14 is used, it may be loaded simultaneously with a fluid 17 which is loaded through a fluid inlet line 34 and mixed by the mixing valve 36 with the enzyme solution 14. Thereafter, the mixture is introduced through the second chamber inlet line 38 through the inlet 40 into the second chamber 30.

In the case a fluid 17 is used, it can include one of several substances. Specifically, the fluid 17 may be a buffer solution which allows dilution of the enzyme solution 14 to specified levels. Thus, if the enzyme solution 14 is highly concentrated, it may be diluted to a level designed to achieve optimized reaction time and product generation. Alternatively, the fluid 17 may be: 1) a higher concentration of the enzyme in enzyme solution 14; or 2) an enzyme solution different from that of enzyme solution 14.

If the fluid 17 is an enzyme like that of enzyme solution 14, the amount supplied can be varied through the mixing valve 36 to selectively adjust the enzyme concentration upwardly in the chamber 30 to achieve optimum reaction time and detectable product generation.

If the fluid 17 is an enzyme different from that of the enzyme solution 14, it may be of the type, for example, designed to achieve a two-stage reaction wherein the enzyme solution 14 catalyzes a reaction to result in an intermediate byproduct. Thus, when the fluid 17 is a second enzyme, it acts on the intermediate byproduct which is then caused to react into a final by product which is detected in the chamber 30 by the signal detector 44.

In FIG. 1 the signal detector 44 is shown located in the second chamber 30, for example, immediately behind the membrane 28 which defines the second chamber 30. In a preferred embodiment, the signal detector 44 is, for example, a signal detecting electrode, preferably of platinum, which when predetermined substances are present in the fluid within the second chamber 30, causes a current to flow from detector 44 through signal detecting electrode lead 52 in a complete circuit with a reference electrode 42. The reference electrode 42 is typically located in the first chamber 26 and is connected through a reference electrode lead 50 to a signal analyzing unit 54.

The signal analyzing unit 54 serves to analyze the signal received and provides an output through an output device 56 which is representative of the amount of the measured component in the sample. The output device 56 is conventional and well known to those of ordinary skill in the art.

For example, the signal analyzing unit 54 and the output device 56 can be, respectively, a conventional personal computer with a monitor and a printer attached thereto. The computer, through the operation of, e.g., conventional glucose analysis software of the type well known to those of ordinary skill in the art, analyzes the current flow from the reference lead 50 and the signal lead 52 to provide a representative output which is indicative of the presence and quantity of a measurable component, i.e., glucose, in the fluid in the chamber 30. Although the reference electrode 42 is shown disposed within the first chamber 26, it can also be disposed within the second chamber 30. As noted, the reference electrode 42 serves to complete the circuit with the signal detecting electrode 44 to detect the presence of the selected material within the second chamber 30.

Of course, if the signal detector 44 is other than an electrode and does not require a reference electrode 42 to complete a circuit, then the reference electrode 42 is eliminated. After the measurement has been conducted, the fluid sample 12 may then be discharged through a first chamber outlet 57 through a sample outlet line 59, through a sample outlet valve 61 and into waste chamber 86. Since some detectable product still remains in the second chamber 30 with enzyme therein, additional enzyme solution 14 is flowed through the chamber 30 to remove all of the detectable components, i.e., by flushing, from the second chamber 30 through an outlet 58.

Optionally as shown in FIG. 1, there is provided a compensating detector 46, when the preferred embodiment is an electrode, which serves to measure signals caused by interfering substances within the fluid sample 12 in the chamber 26. The electrode 46 can optionally have a membrane 28', like membrane 28, disposed around it as shown in dashed lines in FIG. 1. The reason for such an arrangement is to allow rapid removal of interfering substances from the surface of electrode 46 in preparation for the next sample. As noted previously, such signals can be caused by electrochemically active substances such as uric acid, ascorbic acid or acetaminophen present in a sample.

The measurement of the signal caused by the interfering substances is done with the sample which does not yet contain the electrochemically detectable byproduct of an analyte to be measured. While not necessary, if the compensating electrode 46 is employed, the interference signal is subtracted from the signal generated by the signal detecting electrode 44 to provide a true indication of the presence of a measurable component within the chamber 30. As in the case with the reference and signal detecting electrodes 42 and 44, if the compensating detector 46 is an electrode, it is also connected to the signal analyzing unit 54, in this case through compensating electrode lead 48, and the signal detected thereby which is indicative of interfering substances, is processed in a conventional manner by the signal analyzing unit 54 and reflected at the output device 56.

In another embodiment, the reference electrode 42 and/or the compensating electrode 46 can be covered with membranes (not illustrated) of molecular weight cutoffs of about 10,000 g/m. This type of membrane prevents passage of molecules having molecular weights greater than about 10,000 g/m plus or minus known variances as apparent to those of ordinary skill in the art. Thus, when the sample is blood or plasma, such membranes prevent serum proteins of molecular weight greater than 10,000 from contacting the reference electrode 42 and compensating electrode 46, thereby noticeably reducing fouling of electrodes 42 and 46, and in some cases by a significant amount. Of course, membranes having lower molecular weight cutoffs can be employed, depending upon the specific analysis to be conducted. As may be appreciated, the signal detecting electrode 44 is not subject to fouling by the larger molecular weight molecules because it is already protected by the membrane 28 which allows the detectable substances to pass through into the second chamber 30.

It is possible that molecules of molecular weight less than 10,000 g/m pass into chamber 30 through membrane 28 and cause fouling of electrode 44. If this occurs, it is advantageous to short electrode 44 after each measurement is conducted, for example, by closing a switch 41. This has the effect of forcing fouling components off the surface of electrode 44. Likewise, it may also be desirable to short electrode 42 to reduce fouling through the use of a switch 43, as also shown in FIG. 1, in a manner similar to the shorting conducted on the electrode 44.

Figure 2:
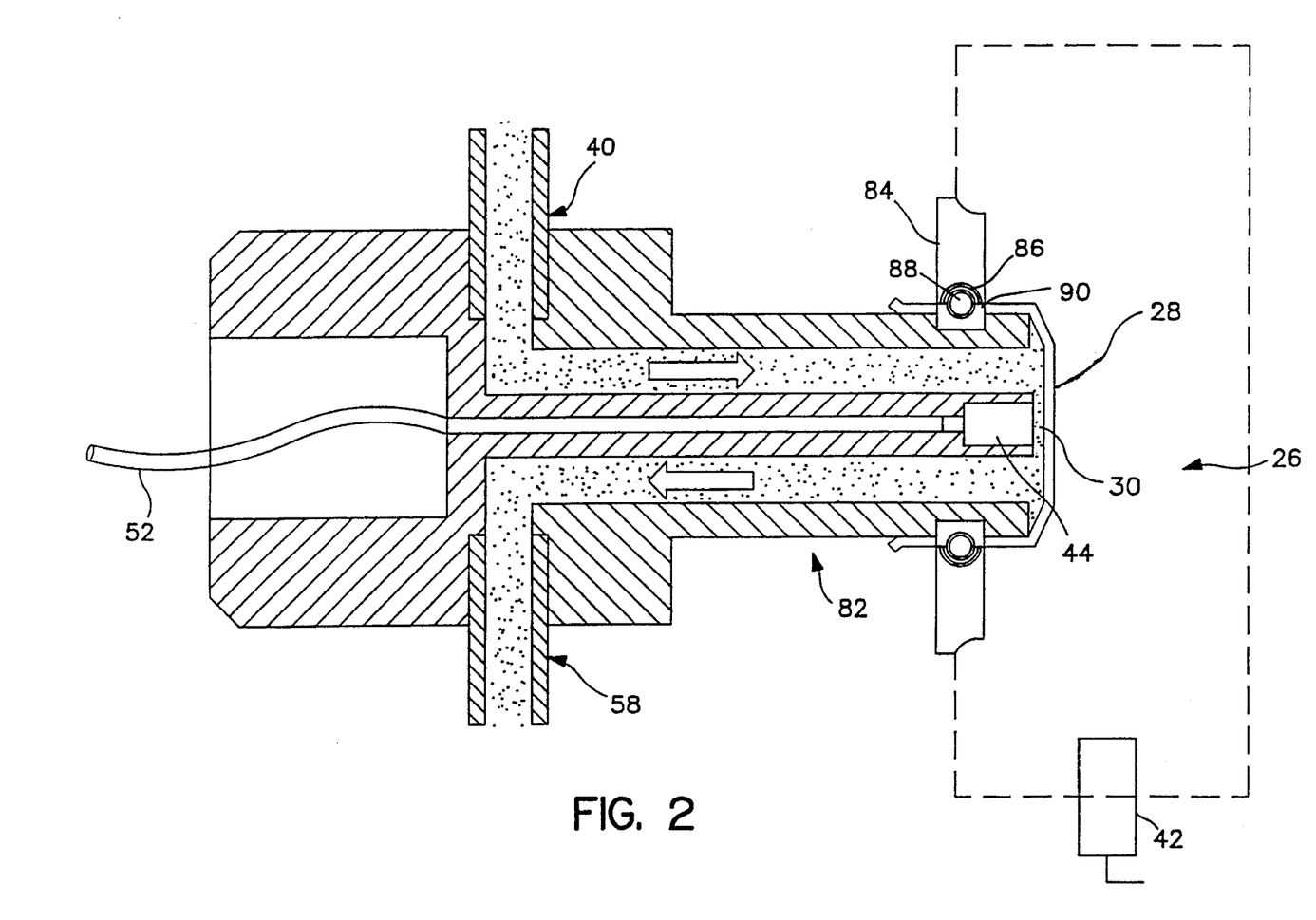
FIG. 2 is a partial, side cross-sectional view of one structure of the device of the invention showing a second measurement chamber with a microflow path thereof, and with a membrane defining the second chamber.

An actual example of one configuration of the second chamber 30 of the system 10 of the invention is shown in FIG. 2. In this embodiment the membrane 28 is held on the end of a projection 82 by means of an O-ring ring 88 received in a groove 90 at the end of the projection 82. Walls 84 which partially define the chamber 26 fit and seal against O-ring 88 at a cut-out region 86 at the end thereof, for example, in a press-fit arrangement, to define the first chamber 26 on the other side of the membrane 28. Alternatives to the press-fit arrangement can include such common variants as a threaded screw fit or other equivalent engagement structures. Thus, as can be seen, the first chamber will be on one side of the membrane 28 and the second chamber 30 will be on the other side of the membrane 28. In this embodiment, the signal detector 44, i.e., a signal detecting electrode, is located within the second chamber 30 and is connected by means of the signal detecting electrode lead 52 to the signal analyzing unit 54, as is shown in FIG. 1.

The electrodes employed for the signal detecting electrode 44, the reference electrode 40 and the compensating electrode 46, which are shown in FIG. 1, are preferably typical electrochemical signal electrodes, more specifically amperometric sensing electrodes, which are useful for the detection of hydrogen peroxide. Such electrodes may include a platinum anode (signal detecting electrode 44) and a silver or a silver/silver chloride cathode (reference electrode 42), with 0.6 positive volts imposed on the platinum electrode. In the case where glucose is being detected at the platinum electrode surface, hydrogen peroxide undergoes catalysis to generate a current proportional to its concentration as follows:

The current so measured is used to calculate the concentration of the preselected analyte in the sample 12, i.e., glucose.

In the embodiment of FIG. 2, the second chamber inlet 40 and a second chamber outlet 58 for enzyme solution preferably are nonporous tubes of conventional construction. The chamber 30 is shown as being relatively small in size when compared to the first chamber 26 for the sample.

For example, in one embodiment where the first chamber 26 can be in the shape of a cup with the second chamber 30 defined by a projection into the cup (FIG. 2), the first chamber 26 volume can be on the order of 500–1000 microliters with the second chamber 30 volume being on the order of about 1/10 to about 1/100 the volume of the first chamber 26. On the other hand, total volume flowing through the embodiment of FIGS. 5–9 will be only about 90 microliters or less, with the volume flow through the first chambers 26a and 26c each making up about 25 microliters, and the volume of the second chamber 30 making up about 7 microliters or less of the total 90 microliters.

Turning again to the embodiment disclosed in FIG. 1, it will be appreciated that while the flushing of chamber 30 is conducted, the components from the sample 12, the carrier or enzyme solution 14 and the fluid 17 are discharged through the second chamber outlet 58, through a second chamber outlet line 60 and through second chamber outlet valve 62a, in some cases directly into a waste container 64. Alternatively, it may be possible to reuse the discharge from the second chamber 30 by recycling because the second chamber 30 is so small relative to the chamber 26 that it may be possible to dilute what are now contaminants in the discharge from the second chamber 30 to non-detectable amounts. In order to recycle, the valve 62a is preferably a three-way valve capable of directing flows to the waste container 64, or into a recycling unit 66.

By recycling, the signal or detectable component can be flushed and diluted to non-detectable amounts, for example, as shown in FIG. 1, by passing the discharge from the second chamber 30 through the discharge valve 62a into a bypass line 68 leading optionally to a removal unit 70 arranged alone or in parallel to a recycling holding tank 78. In the removal unit 70, a removal device 72 serves to eliminate undesired components from the discharged carrier or enzyme solution 14 from the second chamber 30, and passes the carrier or enzyme solution 14 through valve 62d and recycle line 80 to the inlet valve 36, i.e., in this case a four-way valve, and back into the second chamber 30. This avoids the requirement of having to constantly feed fresh enzyme through line 32 thereby significantly reducing costs. In some embodiments such a removal unit 70 is not necessary because the undesired components break down over time before recycling into the second chamber 30.

With respect to the removal device 72, any unit can be used that filters out the undesired components. For example, it is contemplated that to remove hydrogen peroxide an immobilized catalase unit can be employed to cause an enzymatic breakdown of the hydrogen peroxide to ensure that there is no measurable component present, i.e., that any hydrogen peroxide returned to the second chamber 30 is in amounts which are non-measurable by the system. Likewise, a similar result can be accomplished with the recycling holding tank 78 in which the hydrogen peroxide can be reduced in concentration to non-detectable amounts. The various flows are then controlled and directed by valves 62b and 62c, all of which make up a part of the enzyme recycling unit 66 of the embodiment of FIG. 1.

In the case of using the recycling holding tank 78, instead of removing measurable components, the tank 78 is made large enough to ensure that the measurable component becomes sufficiently diluted, therefore the concentration level is sufficiently low so that upon recycling into the second chamber 30 the amount of residual, measurable component remaining is insufficient to affect the detection or measurement being conducted in the second chamber 30.

As also shown in FIG. 1, once the enzyme solution 14 has been used sufficiently to lose its effectiveness, waste line 76 permits discharge of the recycled enzyme through valve 62e into waste container 64. New enzyme can then be added to the system 10 through inlet line 32. An alternative physical embodiment of the analyzer 10 in accordance with the invention is better illustrated in FIG. 3, wherein like elements are numbered the same as in the previous embodiments. In this embodiment the fluid sample 12 is initially mixed with the fluid 17 at the inlet valve 22, and the mixture is thereafter passed through the inlet line 24 and the first chamber inlet 25 into the chamber 26. The interaction of the fluid 17 with the fluid sample 12 results in components of the fluid sample being carried by the carrier solution through means of a chemical or physical bond, or in an intermediate byproduct or final product form, i.e., a signal. Either one of the resulting product passes through the membrane 28 into the second chamber 30, to be detected by the signal detector 44. The carrier or enzyme 14 is passed through the inlet line 32 through the valve 36, into inlet line 38 and through the inlet 40 into the chamber 30. The carrier or enzyme 14 serves as a catalyst reactant with or as a carrier for the byproduct or signal which is introduced into the chamber 30.

Figure 3:
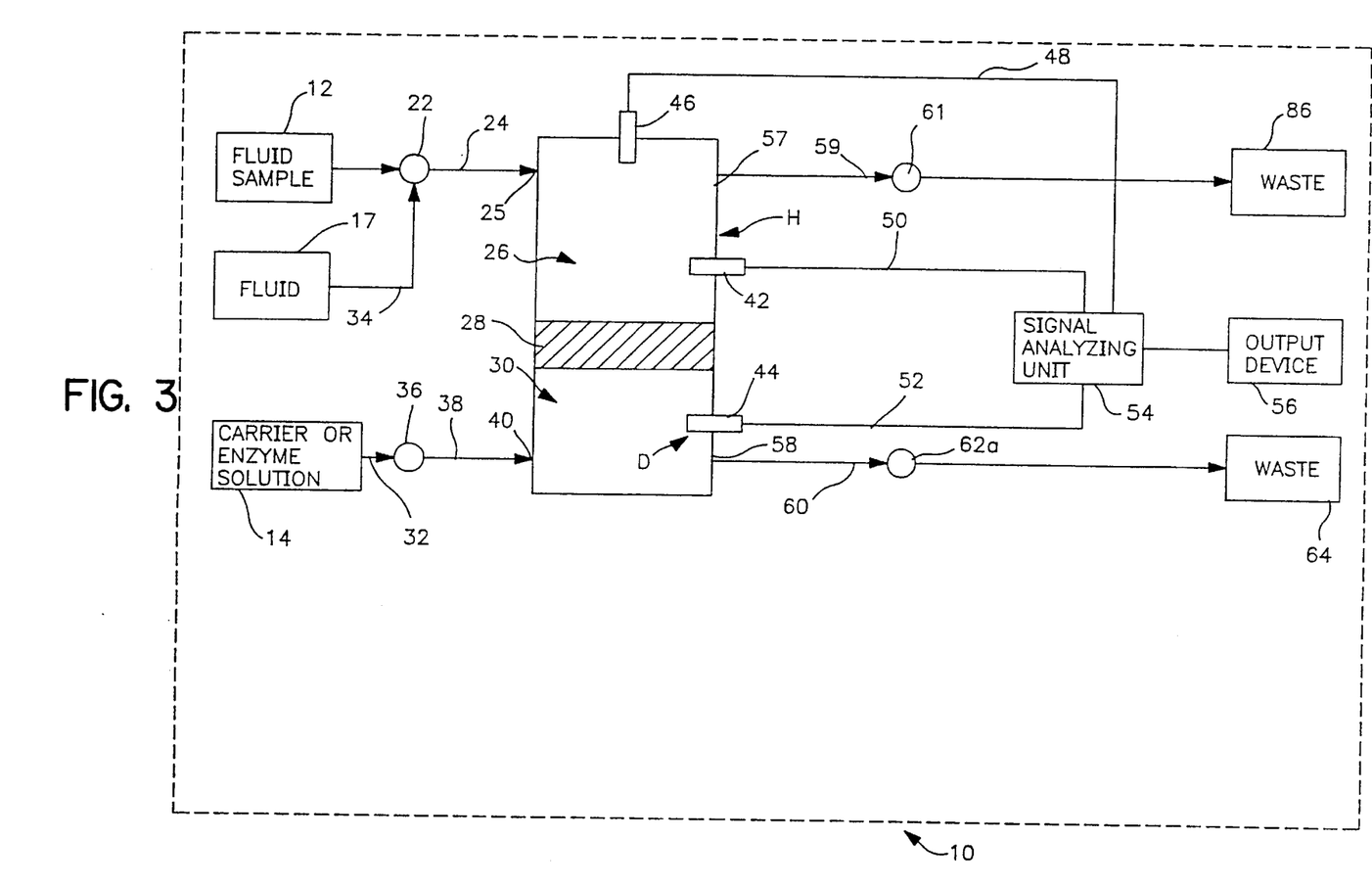
FIG. 3 is a schematic diagram of a second detailed embodiment of the analyzer according to the present invention.

In the chamber 30, in some reactions, the intermediate product passes through the membrane 28 reacts with reactant introduced into the chamber 30 or reacts in the presence of enzyme in the chamber 30, to result in a final product which is detected as the signal.

Alternatively, as previously noted, if the final product has already been generated in the chamber 26, the fluid in the second chamber 30 may then simply be a carrier for the product from the first chamber 26.

Once the desired end-product is detected by signal detector 44, the second chamber 30 is flushed by adding more carrier or enzyme solution 14 and discharging the initial contents through the second chamber outlet 58 through line 60 and second chamber outlet valve 62a into the waste chamber 64. Of course, as may be appreciated, this embodiment may also have a recycling unit similar to the recycling unit 66 of FIG. 1.

Figure 4:
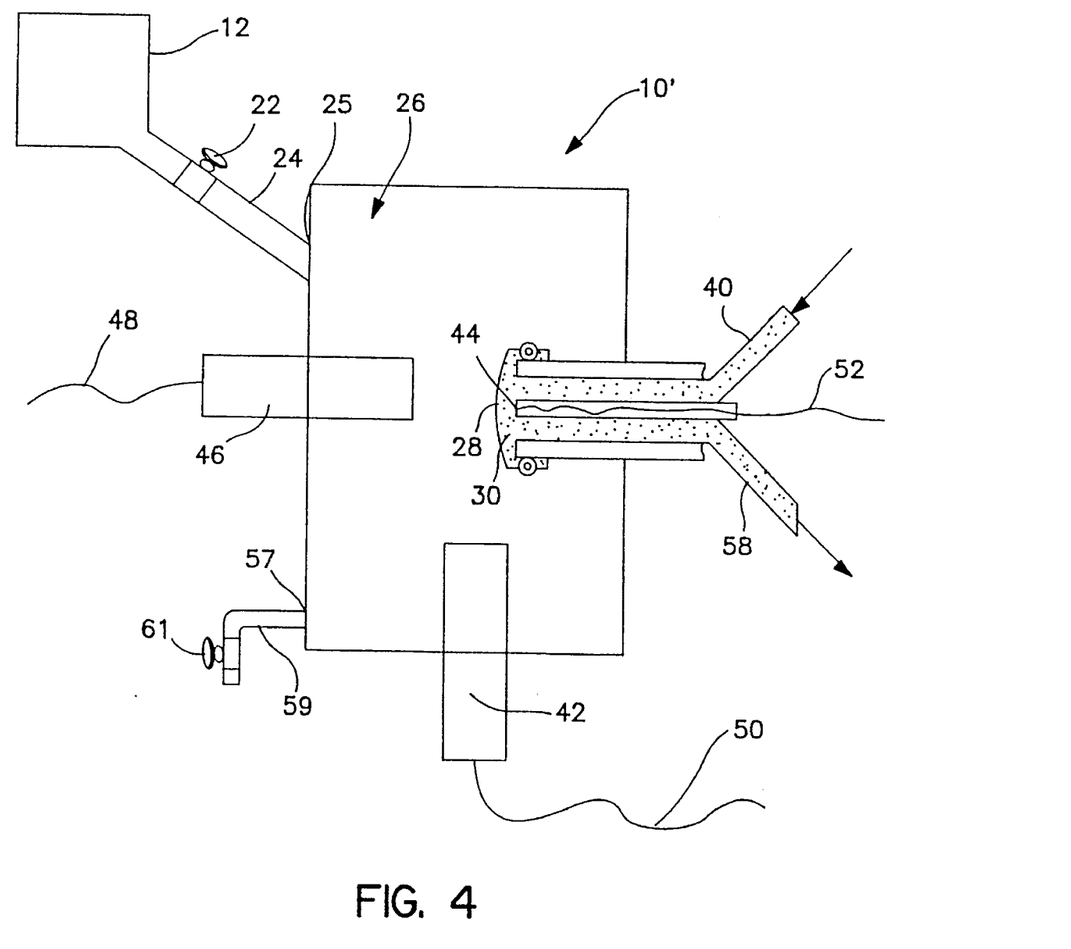
FIG. 4 is a schematic diagram of one embodiment of the system of the invention arranged for conducting analysis of components in a chemical assay.

An alternative embodiment 10' in accordance with the invention is shown in FIG. 4. In this embodiment a sample 12 for a chemical assay is pre-stored as the fluid sample 12. Such a sample can be plasma or serum which is then held as the fluid sample 12. The plasma or serum mixes with an enzyme capable of catalyzing a reaction involving glucose as a substrate to yield hydrogen peroxide. After a predetermined, i.e., calibrated, amount of time, the inlet valve 22 is opened and the fluid sample 12 flows through the inlet line 24 and the first chamber inlet 25 into the first chamber 26. The hydrogen peroxide previously generated in the sample 12 then passes through the membrane 28 into the fluid in the chamber 30 to be carried thereby and detected by the signal detecting electrode 44. Upon detection by the signal detecting electrode 44 and reference electrode 42, a signal is passed through the leads 50 and 52, to the signal analyzing unit 54 (not shown in this figure), as previously described.

The fluid in chamber 30, which is supplied through inlet 40 and discharged through outlet 58 in this embodiment need not be enzyme and only needs to be a fluid capable of carrying the byproduct of the fluid sample 12, i.e., the hydrogen peroxide generated in the sample 12. The hydrogen peroxide detected is indicative of the amount of an analyte in the blood sample, and depending upon the nature of the sample 12, it may be necessary to take into account the concentration of enzyme and time of holding of fluid sample 12. Alternative samples may be used to detect other components as will be readily apparent to those of ordinary skill in the art.

After the measurement is conducted, the sample fluid 12 can be discharged through the first chamber outlet 57 and the sample outlet line 59 by opening the sample outlet valve 61. Further, as in the case with the previously described embodiments, a compensating electrode 46 can also be provided to measure interfering substances and adjust for the measurements made by the electrodes 42 and 44.

With respect to the fluid in the chamber 30, as previously noted, the fluid is preferably one of several carrier fluids, all capable of carrying in suspension or solution, the final detectable product, for example, any hydrogen peroxide generated in the fluid sample 12. Specifically, once the sample 12 is introduced into the chamber 26, hydrogen peroxide passes through the membrane 28 into the chamber 30 to be detected by signal detector 44. After the measurement has been conducted, the fluid sample 12 is discharged through the first chamber outlet 57 and a new sample 12 is introduced through the first chamber inlet 25. Likewise, the fluid in the chamber 30 having hydrogen peroxide therein is discharged through the second chamber outlet 58 to remove any detectable hydrogen peroxide and the second chamber 30 is refilled through the second chamber inlet 40. Although this embodiment has been described with reference to measurement of analyte levels in blood such as glucose, it will be appreciated that the system can be employed to measure other components of blood such as triglycerides, etc. Alternatively, in FIG. 4, the fluid in chamber 30 can be one capable of causing a reaction of the substance in the sample 12 which is the first product of a reaction in the sample 12 and results in a third substance which is then detected in the chamber 30.

Another alternative embodiment 10" of the device of the invention is shown in FIGS. 5–9. The device of FIGS. 5–9 takes advantage of the fact that electrochemical detection of specified components requires only very small amounts of fluid, i.e., liquid. The amount of liquid required is an amount sufficient to merely "wet" the surface of the electrodes. By "wet" the surface of the electrode is meant an amount sufficient to achieve electrochemically measurable activity which is accurately indicative of the amount of substance being measured. Such a "wetting" is all that is required in all embodiments of the invention. Thus, in the case of the device of FIGS. 5–9, both the amount of enzyme or carrier fluid as well as the amount of sample required to practice the invention can be substantially reduced because the device of FIGS. 5–9 can be made of a substantially smaller size than the other embodiments described herein.

Figure 5:
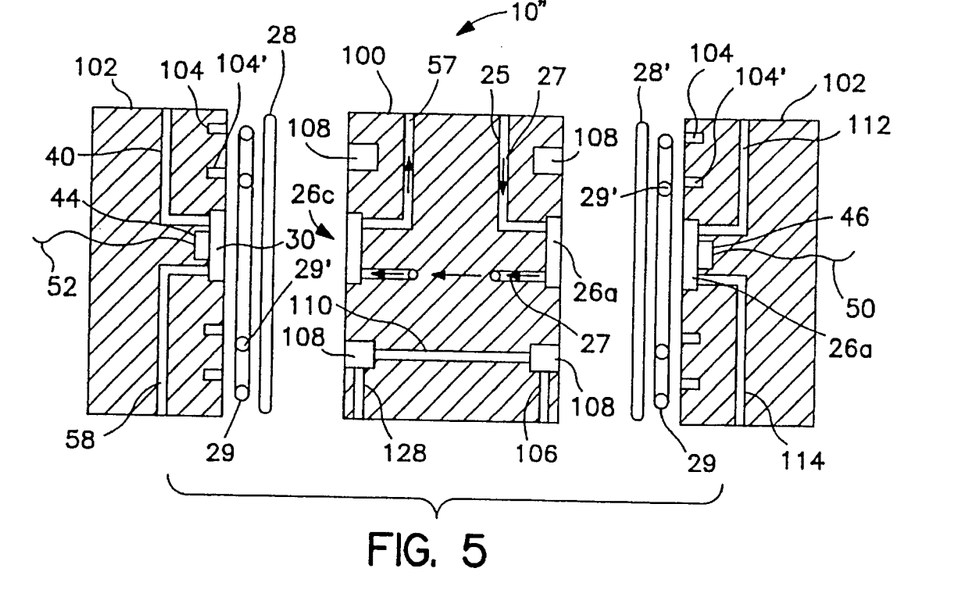
FIG. 5 is a side cross-sectional view, in exploded form, of an alternative embodiment of the analyzer of the invention, shown with numerous small chambers designed to minimize the volumes of samples and enzyme or carrier solution required to practice the invention.
Figure 6:
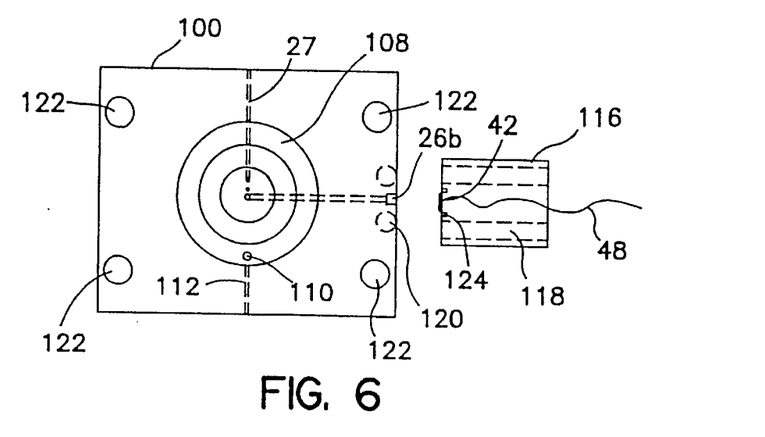
FIG. 6 is a side view of the center block of FIG. 5 showing the end cap of the device (not shown in FIG. 5) in exploded form with portions located within the body thereof shown in phantom-broken lines.
Figure 7:
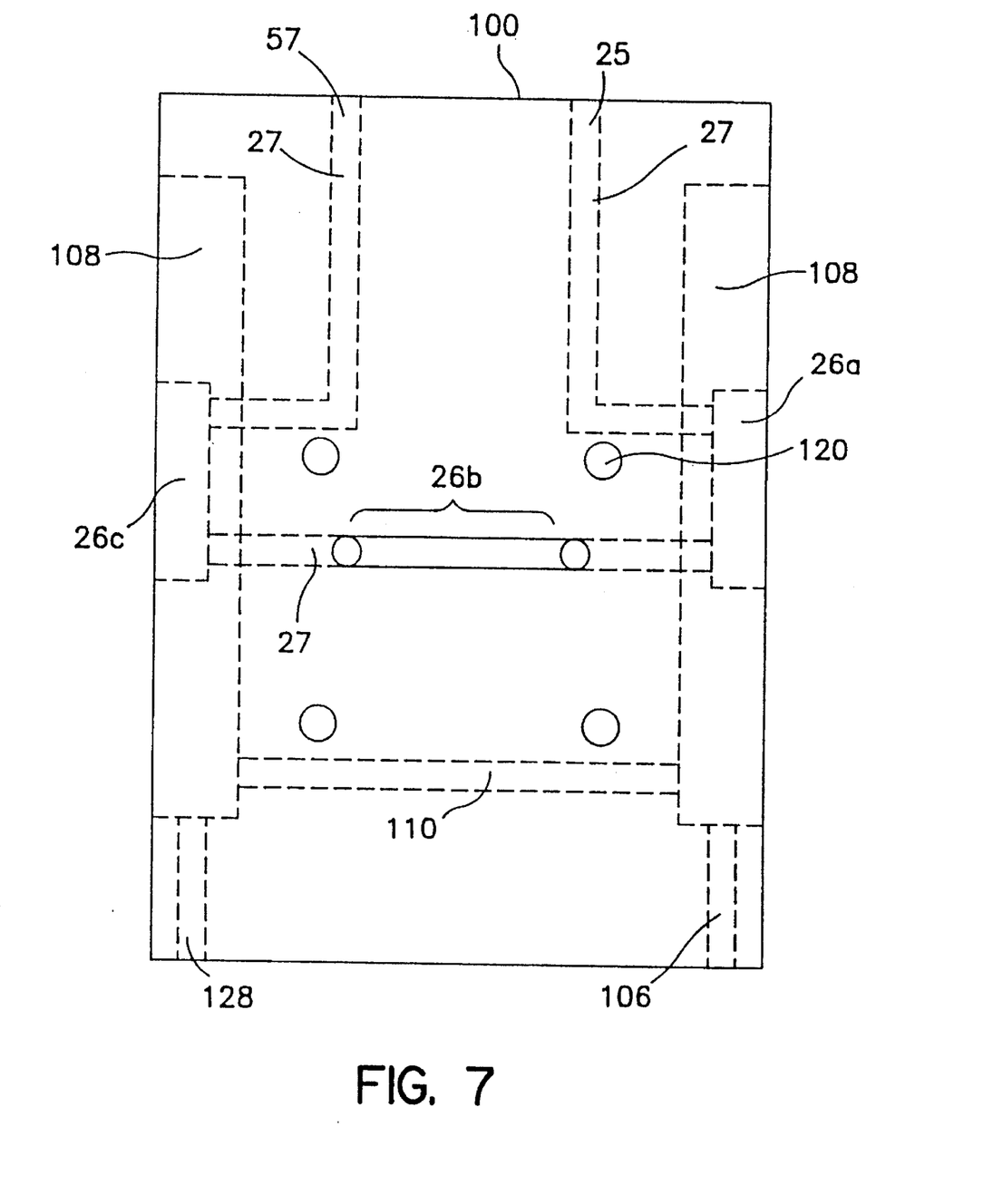
FIG. 7 is a view of the center block of FIG. 7, showing in phantom-broken lines some of the features shown in the cross-sectional view of FIG. 5.
Figure 8:
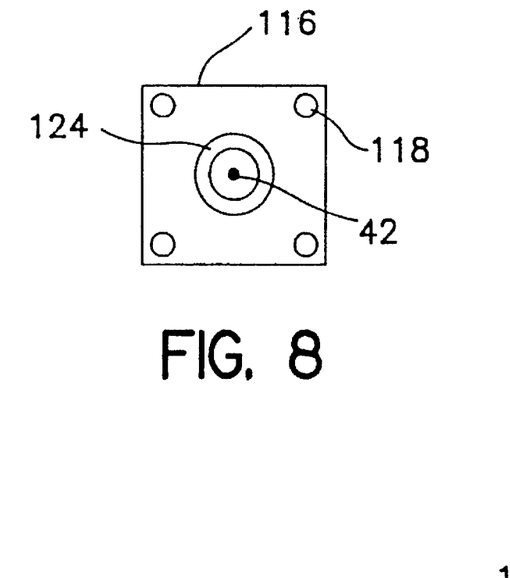
FIG. 8 is a front view of the end cap of FIG. 5 (the side that abuts against the center block), showing an electrode used as a reference electrode.

FIG. 5 shows the alternative embodiment of the invention in side cross-section, exploded view. A fluid sample is introduced through the first chamber inlet 25 to pass into multiple miniature first chambers 26a, 26b (FIG. 6), and 26c. In the first instance, the flow of the fluid sample is into chamber 26a, and passes through membrane 28' into contact with the compensating electrode 46 which is located in a third chamber 26a' on the other side of membrane 28'. Inside the third chamber 26a', typically a buffer solution is typically located which serves to carry interfering substances to be detected by the compensating electrode 46. The first chambers 26a and 26c are defined by two side blocks 102 which abut against center block 100 with O-rings 29' fitting in a corresponding groove 104' in each of the side blocks 102 to seal the chambers 26a and 26c. First chamber 26a is further defined by membrane 28' which also serves to define third chamber 26a'. From the chamber 26a the sample continues through flow path 27, as better illustrated by FIGS. 7 and 8, into a second chamber 26b which, as shown in FIG. 6, is defined by end block 116 abutting against the center block 100. As in the case with side block 102, an O-ring (not shown in this case) is seated within groove 124 when the system is assembled to seal second chamber 26b. The fluid sample then passes through chamber 26b in contact with reference electrode 42 for completing a circuit with a detecting signal electrode 44 discussed hereafter.

Figure 9:
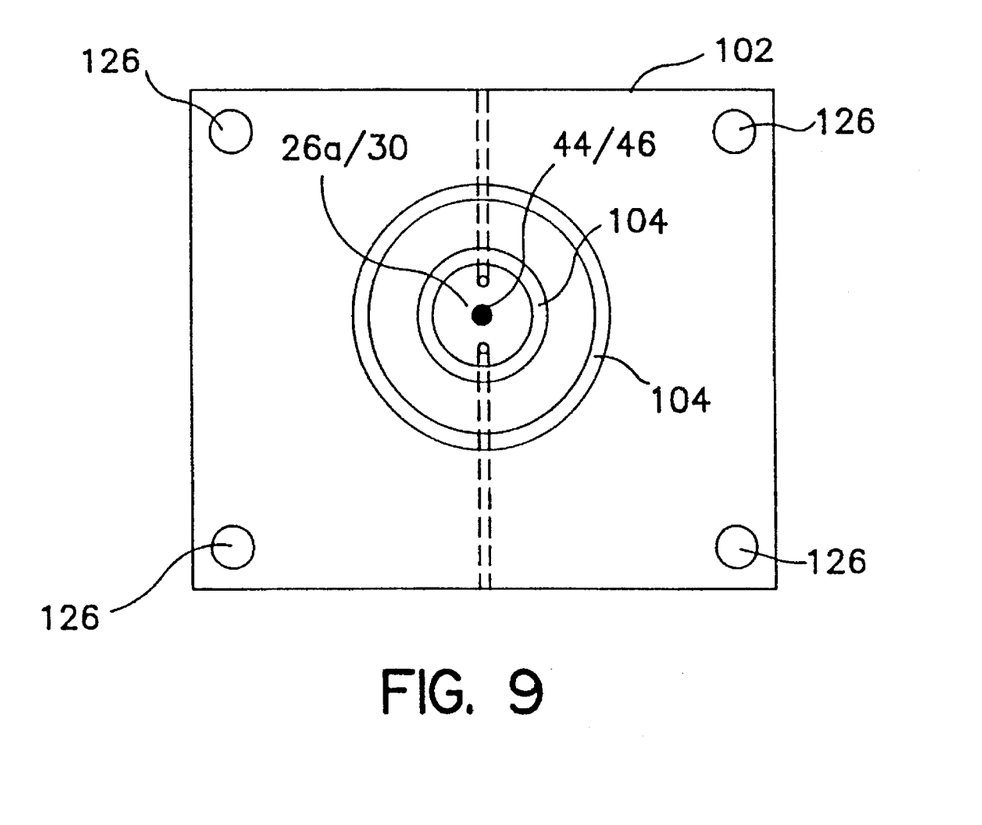
FIG. 9 is a side view of the side caps of FIG. 5 (both side caps being identical) showing a portion that abuts against the center block of the system.

From chamber 26b, the fluid sample continues through the flow path 27 into the chamber 26c and into contact with the membrane 28 which defines the second chamber 30. As may be appreciated from FIG. 5, the O-ring 29 along with the O-ring 29' engage in their corresponding grooves 104 and 104' when the device is assembled, and serve to hold the membrane 28 in position to define the second chamber 30. The measurable component in the sample then passes through the membrane 28 to be carried by a carrier solution in the chamber 30 and detected by the signal detecting electrode 44, or to react in the presence of an enzyme in the chamber 30 to result in a product detectable by the signal detecting electrode 44. The entire assembly is held together by screws which fit respectively in and through openings 118, 120, 122 and 126 as shown in FIGS. 6 and 9.

After the detection step is conducted, the enzyme or carrier solution with the detectable product can then be flushed from the system by adding carrier or enzyme through the inlet 40 into the second chamber 30 thereby discharging the spent carrier or enzyme through the outlet 58. Likewise, the system can be flushed and a baseline value set for the compensating electrode 46 and the reference electrode 42. The membrane 28' defines the third chamber 26a' in which the enzyme or carrier solution with the detectable product are located after conducting a measurement. The system is flushed and a baseline value set for the compensating electrode 46 and the reference electrode 42 by flowing a buffer solution through the inlet 25 and the outlet 57 and by also introducing a buffer solution through inlet 112 which is passed through third chamber 26a' and out discharge 114 to flush interfering substances from the third chamber 26a'.

In order to provide more accurate or more exacting control of any reaction caused for the measurement of preselected components, temperature control can be effected with the device of FIGS. 5–9 by introducing hot or cold liquid, e.g., water, into an annular ring, i.e., a water jacket, thereof. As illustrated in FIGS. 5 and 6, the water is introduced through an inlet 106 from which it passes into annular rings 108 which are interconnected by a passageway 110. In the rings 108 the water surrounds the chambers 26a and 26c to provide heating or cooling as well as to heat or cool the entire assembly 10. As may be appreciated, the O-rings 29 and 29' also serve to seal the annular rings 108 by fitting into the grooves 104 and 104' to prevent leakage of liquid therefrom. As the liquid circulates it is then discharged through an outlet 128.

With respect to the various fluids employed in the invention, it is noted that the fluid sample in general can be a multi-component mixture which is made up of a liquid, and typically, at least one analyte which is distinct from the liquid, and is carried therein. The liquid of the fluid sample can be, for example, a single-phase system such as a single liquid, or a solution of two or more miscible liquids, or a multi-phase system such as an emulsion. The analyte in the sample can be, for example, a chemical compound such as a carbohydrate, a lipid, or a protein. The fluid sample typically can also include suspended cells or cellular material, for example, blood or lysates, solid particles such as food pulp, or dissolved solids such as sugars or salts.

As can be appreciated from the background discussion set forth previously, a preferred use of the device in accordance with the invention is with biological or physiological fluids, such as blood or a blood portion such as plasma. Other physiological or biological fluids which can have quantitative measurements of components thereof measured with the device of the invention include urine, saliva, cell lysates, tissue cultures and culture media. Alternatives to such biological or physiological fluids include consumable liquids such as fruit juices, soft drinks, milk, as well as non-consumable liquids, typically, liquid product streams such as treated waste water.

Typical enzyme and other solutions employed in the apparatus and method of the invention include a liquid carrier, which is conventional and well known to those of ordinary skill in the art, such as water, or a saline solution, and with the enzyme system including one or more enzymes which are capable of interacting with the preselected analyte to ultimately produce a byproduct which is detected in the device and method of the invention. For purposes of this disclosure, the byproduct will be described hereafter as being a detectable signal.

In the case where the enzyme system is made up of a single enzyme, the enzyme interacts with the preselected analyte to produce the detectable signal directly. Depending on the particular single enzyme employed for production of a detectable signal, the enzyme system can also include cofactors and/or additional substrates necessary for production of detectable signal.

Alternatively, the enzyme system can include two or more enzymes characterized by causing coupled enzymatic reactions which sequentially or simultaneously result in the byproduct which is the detectable signal. Such is the case in the embodiments of FIGS. 1, 2, and 3 where the fluid 17 is an enzyme and the carrier or enzyme solution 14 is a different enzyme. In such a multi-enzyme system, the first enzyme produces an intermediate byproduct through reaction with the preselected analyte to produce the intermediate byproduct. The byproduct then interacts with the second enzyme as a substrate or cofactor to produce, in turn, the byproduct which is the detectable signal. As may be appreciated by those of ordinary skill in the art, while the invention is, in this specific example, discussed with reference to a double enzyme system, in reality, the number of enzyme systems or enzymes employed in the system is unlimited, with the only limitations being the time of reaction and ultimate ease of use within the apparatus and method of the invention.

In some cases, the detectable product is already present in the sample because it was originally present or because it was generated elsewhere, and need not be generated. When this occurs, no enzyme is necessary for the measurement chamber 30 and only a carrier solution such as a buffer need be provided to carry the detectable substance.

The detectable signal in practicing the invention depends on the nature of the analyte and the selected enzyme system. For example, the signal can be an electrochemically detectable product, such as hydrogen peroxide, which is detectable by, for example, platinum electrodes.

Alternatively, the signal can be an optical signal such as a color change or a fluorescent signal, i.e. a photon emission, as will be readily apparent to those of ordinary skill in the art. In the case of enzyme systems used to generate hydrogen peroxide, it is noted that such systems allow for electrochemical, optical as well as fluorescent signal detection. The optical and fluorescent signal detection can be effected by reacting hydrogen peroxide with additional compounds giving rise to chromogens or fluorogens which are detectable by fluorescent techniques.

An example of color change is a reaction where the amount of analyte present is proportional to the intensity of color change as follows:

$2H_2O_2$ + 4-Aminoantipyrene + p-Hydroxybenzene

Sulfonate $\xrightarrow{\text{Peroxidase}}$ $4H_2O$ + Quinoneimine

Figure 10:
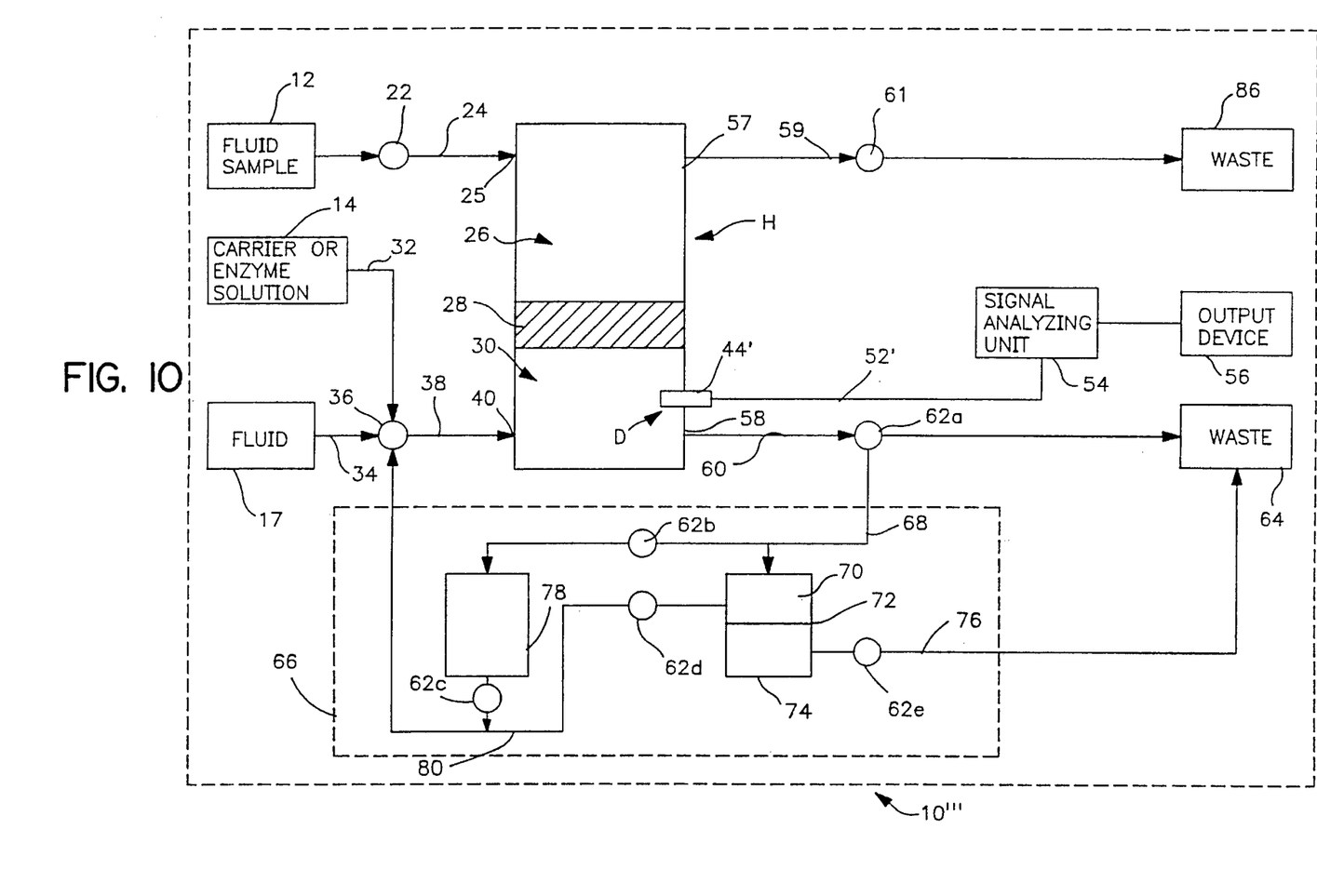
FIG. 10 is a schematic diagram of a detailed embodiment of an analyzer of the invention like that of FIG. 1, but using optical detection in place of electrochemical detecting.

An optical detection system can be implemented as shown in FIG. 10, which is similar to FIG. 1. In this embodiment the electrodes 42 and 46, and their associated components are eliminated. A color, fluorescence, or luminescence detector 44' replaces electrode 44, and is connected through lead 52' to the signal analyzing unit 54. Although detector 44' is shown within the chamber 30, it will be appreciated that other equivalent configurations can be employed. One example of an alternative is with detector 44' located outside of the wall of chamber 30. In such a construction the wall of chamber 30 can be transparent to allow detection to occur.

In selecting the particular enzyme system to be employed, it is important to consider stability, the presence of one or more enzymes in the enzyme system, or one or more intermediate substrates therefor in the fluid sample. Other factors include fluid sample properties, including pH, enzyme rate profiles and costs.

An example of a single-enzyme system is glucose oxidase. As discussed previously, glucose oxidase interacts with glucose (the preselected analyte) which passes through the membrane into the measurement chamber and generates hydrogen peroxide as the detectable signal. The hydrogen peroxide thus generated can then be directly detected by an electrochemical signal detector, i.e., an electrode pair, as discussed previously.

An example of a useful multi-enzyme system is the lipase/glycerol kinase/glycerol-1-phosphate oxidase system. Lipase interacts with triglycerides, the preselected analyte, to generate glycerol. Glycerol in turn serves as a substrate for glycerol kinase. Interaction of glycerol and glycerol kinase, together with an ATP molecule, yields glycerol-1-phosphate, which serves in turn as the substrate for glycerol-1-phosphate oxidase. This final enzymatic reaction affords hydrogen peroxide as the detectable signal.

An alternative to amperometrically detectable systems are exemplary enzyme systems which generate optically detectable signals and include the glucose oxidase/horseradish peroxidase system. In this system, the hydrogen peroxide generated by glucose oxidase upon interaction with glucose, as described above, is subsequently acted upon by horseradish peroxidase. In combination with a suitable additional peroxidase substrate, the horseradish peroxidase produces a color change as the detectable signal. The suitable additional peroxidase substrates include ortho-phenylenediamine (OPD), 2,2-azino-di-(3-ethylbenzthiazoline sulfonic acid-6) diammonium salt (ABTS) and 3,3',5,5'-tetramethylbenzidine (TMB). These and other suitable peroxidase substrates are described in Voller et al., *Manual of Clinical Laboratory Immunology*, Chapter 17.

For use as the membranes 28 and 28' which define the second chamber and third chambers, a dialysis membrane which is permeable to a spectrum of test molecules is preferred. Selection can be accomplished by studying the actual dialysis rates of solutes of known size under standard conditions. This selection technique is conventional and well known to those of ordinary skill in the art.

Specific examples of the membranes that can be used with this invention include those which are commercially available and are manufactured by Spectrum Medical Industries, Inc., of Los Angeles, Calif., under the trade name Spectra/Por. Such membranes are typically made of natural cellulose. Numerous membranes are available with various molecular weight cutoffs ranging from 1,000 to 50,000 g/m, and in some cases contain glycerine which is added as a humectant and plasticizer. The selection of membranes can be made conventionally depending on the size molecule desired to be diffused when conducting the method of the invention.

Having generally described the invention, the following are specific examples of the use of the device to detect certain substances in a fluid sample.

EXAMPLES

It was desired to detect glucose in both body and nonbody fluids. The following are examples of tests conducted on plasma, whole blood, orange juice, Coca-Cola soft drink, grapefruit juice, Diet Coca-Cola soft drink, Hawaiian Punch fruit drink and Peach Snapple fruit drink. In all these experiments it was desired to detect glucose. In this regard, it is noted that glucose is not detectable amperometrically. Thus, in all cases there was a conversion to gluconic acid and $H_2O_2$ through reaction in the presence of glucose oxidase. Detection of the resulting hydrogen peroxide yielded a signal proportional to the glucose quantity.

EXAMPLE 1

This test was conducted for biological fluids utilizing the embodiment of FIG. 5. The fluids tested were plasma and whole blood. The same fluids were also tested using the YSI 2300 STAT glucose analyzer, commercially available from Yellow Springs Instruments, Inc., of Yellow Springs, Ohio, which employs an immobilized/trapped enzyme system, and the results were compared to those achieved using the embodiment of FIG. 5.

In detecting glucose, the following reaction takes place:

The detection system consisted of a platinum anode and a silver or a silver/silver chloride cathode, which in the case of the embodiment of the invention used in this example, had 0.6 volts imposed across the electrodes. Thus, using this system at the platinum electrode (anode), the following reaction then took place to result in a current proportional to the concentration of glucose:

In using the system of FIG. 5, the detecting electrode in the second chamber had glucose oxidase enzyme microflowed in front of it on one side of the membrane. A plasma or whole blood solution was prepared by dilution with PBS in a ratio of 1:20. The diluted plasma and the whole blood, for each test respectively, was introduced into the first chamber 26 and the detecting electrode 44 detected a signal proportional to the amount of glucose in the plasma and the whole blood, respectively, as shown in Table 1 below. Portions of the same samples were also tested using the above-referenced YSI 2300 STAT glucose analyzer following the conventional instructions outlined for its use. The results of all the tests are outlined below in Table I.

TABLE I

| SAMPLE | NO. OF TESTS | FIG. 5 SENSOR | YSI |
|---|---|---|---|
| Plasma 1 | 3 | 84 | 81 |
| Plasma 2 | 3 | 61 | 64 |
| Plasma 3 | 3 | 81 | 81 |
| Whole Blood 1 | 2 | 70 | 68 |
| Whole Blood 2 | 3 | 53 | 53 |
| Whole Blood 3 | 3 | 67 | 67 |

(Glucose (mg/dL))

It will be appreciated from the above table that the results achieved using the system of the invention did not differ significantly from the results using the YSI 2300 device.

As can be appreciated, both the system of the invention and the YSI device function effectively to measure glucose in a biological sample. However, in the case of the YSI device, recalibration was required every fifteen minutes, or every five tests, whichever occurred first. In accordance with the invention, this requirement was avoided by shorting the electrodes after each measurement, for example, in a manner similar to that illustrated in FIG. 1.

In addition, since the enzyme in the YSI device was immobilized, it had a shelf life of only about two weeks, requiring a replacement operation which in turn requires recalibration of the system, a time consuming process. Further, if during calibration, a shift of the baseline of over 2% occurred, then it was necessary to restart the calibration procedure. As can be appreciated, all of the above factors result in significantly reduced throughput and complications in operation of the YSI device when compared to the system and method of the invention.

EXAMPLE 2

This test was similar to the tests conducted in Example 1. The fluids tested were orange juice, Coca-Cola soft drink, grapefruit juice, Diet Coca-Cola soft drink, Hawaiian Punch fruit drink and Peach Snapple fruit drink. In the embodiment of FIG. 5, a detecting electrode in second chamber 30 was microflowed with glucose oxidase and the background electrode was microflowed with a diluent, i.e., PBS, to establish a background signal level. A portion of each sample was respectively introduced into first chamber 26 of 25 µl of the fluid diluted with 475 µl of buffer solution. The compensating electrode detected no background signal. Portions of the samples were also tested with the YSI 2300 STAT glucose analyzer following the procedures outlined therefor. The results obtained are shown in Table II below.

TABLE II

| SAMPLE | Glucose (mg/dL) | |
|---|---|---|
|  | SENSOR | YSI |
| Orange Juice | 209 | 211 |
| Coca-Cola | 407 | 415 |
| Diet Coke | 11 | 0 |
| Grapefruit Juice | 408 | 420 |
| Hawaiian Punch | 516 | 517 |
| Peach Snapple | 507 | 522 |

Although the results obtained with the embodiment of FIG. 5 and the YSI device are comparable in terms of glucose values, the YSI device suffered from the complications identified with reference to Example 1.

What is claimed is:

1. An apparatus for measuring the amount of a measurable substance in a sample, comprising:

first chamber means having an inlet and an outlet for having a sample introduced thereinto and removed therefrom, said first chamber means having three chambers interconnected by a flow path, two of said three chambers each have an electrode disposed therein, each chamber being of a size sufficient only for wetting their respective electrodes by an amount sufficient to conduct electrochemical detection of substances;

membrane means partially defining second chamber means located relative to said first chamber means for allowing a first predetermined substance in said sample to pass therethrough;

detecting means disposed in said second chamber for detecting one of said first predetermined substance and a product thereof which comprises a second predetermined substance, in said second chamber; and said second chamber means having an inlet and an outlet for supplying and removing from said second chamber a third substance capable of carrying in suspension at least one of said first predetermined substance and said second predetermined substance, while being retained in said second chamber by said membrane, and for flushing said second chamber means, whereby one of said first and second substances is the measurable substance and said inlet and outlet means allowing flushing of said second chamber after measurement of said measurable substance has been conducted.

2. The apparatus as in claim 1 wherein said inlet means and outlet means of said second chamber means are for supplying and removing an enzyme from said second chamber means.

3. The apparatus as in claim 1 wherein said detecting means is an electrode and said second chamber means is only of a size sufficient to wet said electrode to allow electrochemical detecting to occur.

4. The apparatus as in claim 1 further comprising means for detecting substances which interfere with detection of predetermined substances to be detected.

5. The apparatus as in claim 4, further comprising a third chamber having said means for detecting substances which interface with detection of predetermined substances to be detected, a second membrane defining at least one wall of said third chamber for allowing said substances which interfere to pass therethrough into said third chamber, and buffer inlet means and buffer outlet means for flushing said third chamber of said substances which interfere after each measurement.

6. The apparatus as defined by claim 5 wherein said measurement chamber has a volume less than about 100 microliters.

7. The apparatus as in claim 1 further comprising means for receiving a signal from said detecting means and for processing said signal and generating an output indicative of the amount of predetermined substance in a sample being analyzed.

8. The apparatus as in claim 1 wherein said second chamber means has an electrode disposed therein and is separated from said chamber of said first chamber means having no electrode by a permeable membrane, and wherein said second chamber means is of a size only sufficient to wet said electrode therein an amount sufficient to conduct electrochemical detection of substances.

9. The apparatus as in claim 1 further comprising heating means for controlling the rate of any reactions conducted therein.

10. The apparatus as in claim 1 further comprising buffer inlet means for injecting buffer solution into said first chamber means, and buffer outlet means for removing buffer solution from said first chamber means.

11. An apparatus for measuring the amount of an analyte in a fluid sample, said apparatus comprising (a) a housing defining a sample-receiving chamber and a measurement chamber separated by a semipermeable membrane, said sample-receiving chamber having an inlet for admitting said fluid sample into said sample-receiving chamber, said membrane transmitting said analyte from said sample-receiving chamber to said measurement chamber, said measurement chamber containing an enzyme which reacts with said analyte to produce a measurable byproduct, and (b) a detector for detecting said measurable byproduct, said apparatus being characterized in that:

a) said measurement chamber has a volume of less than 1.00 microliters and has an inlet for selectively admitting said enzyme into said second chamber;

b) said detector is positioned within said measurement chamber;, and c) means are provided for flushing said measurement chamber of said analyte, enzyme and/or byproduct.

12. The apparatus as defined by claim 11 further characterized in that a second detector is arranged in said sample-receiving chamber, and circuit means are provided for compensating the output of the detector positioned within said measurement chamber with the output of said second detector.

13. The apparatus as defined by claim 11 further characterized in that said second detector is surrounded by a second semipermeable membrane.

14. The apparatus as defined by claim 11 further characterized in that heating means are provided within said housing for controlling the rate of any chemical reaction within said measurement chamber.

* * * * *